US009592233B2

(12) United States Patent
Myung et al.

(10) Patent No.: US 9,592,233 B2
(45) Date of Patent: Mar. 14, 2017

(54) PHARMACEUTICAL COMBINATION DRUG

(71) Applicant: Boryung Pharmaceutical Co., Ltd., Seoul (KR)

(72) Inventors: Jayhyuk Myung, Seoul (KR); Kyung Wan Nam, Gunpo-si (KR); Cheol Woo Lee, Suwon-si (KR); Ju Won Kim, Seoul (KR)

(73) Assignee: Boryung Pharmaceutical Co., Ltd., Seoul (KR)

( * ) Notice: Subject to any disclaimer, the term of this patent is extended or adjusted under 35 U.S.C. 154(b) by 0 days.

(21) Appl. No.: 14/774,927

(22) PCT Filed: Mar. 14, 2014

(86) PCT No.: PCT/KR2014/002178
§ 371 (c)(1),
(2) Date: Sep. 11, 2015

(87) PCT Pub. No.: WO2014/142607
PCT Pub. Date: Sep. 18, 2014

(65) Prior Publication Data
US 2016/0022679 A1 Jan. 28, 2016

(30) Foreign Application Priority Data

Mar. 14, 2013 (KR) ........................ 10-2013-0027114

(51) Int. Cl.
*A61K 31/513* (2006.01)
*A61K 31/505* (2006.01)
*A61K 31/133* (2006.01)
*A61K 9/20* (2006.01)

(52) U.S. Cl.
CPC .......... *A61K 31/513* (2013.01); *A61K 9/2013* (2013.01); *A61K 9/2018* (2013.01); *A61K 9/2027* (2013.01); *A61K 9/2054* (2013.01); *A61K 31/133* (2013.01); *A61K 31/505* (2013.01)

(58) Field of Classification Search
CPC .. A61K 31/133; A61K 31/505; A61K 31/513; A61K 2300/00
See application file for complete search history.

(56) References Cited

U.S. PATENT DOCUMENTS

| 5,260,440 A | 11/1993 | Hirai et al. | |
|---|---|---|---|
| 2005/0080134 A1* | 4/2005 | Niddam-Hildesheim | C07D 239/42 514/548 |
| 2012/0264772 A1* | 10/2012 | Kim ................... | A61K 31/4422 514/269 |
| 2013/0028974 A1* | 1/2013 | Kim ...................... | A61K 45/06 424/465 |

FOREIGN PATENT DOCUMENTS

| CN | 102485228 A | 6/2012 | |
|---|---|---|---|
| KR | 960005951 B1 | 5/1996 | |
| KR | 10-2011-0097168 A1 | 8/2011 | |
| KR | 10-1058284 B1 | 8/2011 | |
| KR | 10-2011-0126020 A | 11/2011 | |
| KR | 10-1168136 B1 | 7/2012 | |
| KR | 10-2012-0117986 A | 10/2012 | |
| WO | 2011/060945 A2 | 5/2011 | |
| WO | WO 2011060945 A2 * | 5/2011 | ........... A61K 9/1635 |
| WO | 2011/090323 A2 | 7/2011 | |

OTHER PUBLICATIONS

Raquel Dina et al., "Angiotensin II-receptor antagonists: An overview", Am J. Health-Syst. Phar, Jul. 1, 2000, pp. 1231-1241, vol. 57, No. 13.
International Searching Authority, International Search Report for PCT/KR2014/002178 dated Jun. 27, 2014.

* cited by examiner

*Primary Examiner* — Michael B Pallay
(74) *Attorney, Agent, or Firm* — Sughrue Mion, PLLC

(57) ABSTRACT

Provided is a pharmaceutical combination preparation including fimasartan and rosuvastatin as active ingredients together with meglumine. The combination preparation exhibits an outstanding effect in treating cardiovascular disease by improving the disintegration and the dissolution which obtained better drug bioavailability and drug safety.

20 Claims, 1 Drawing Sheet

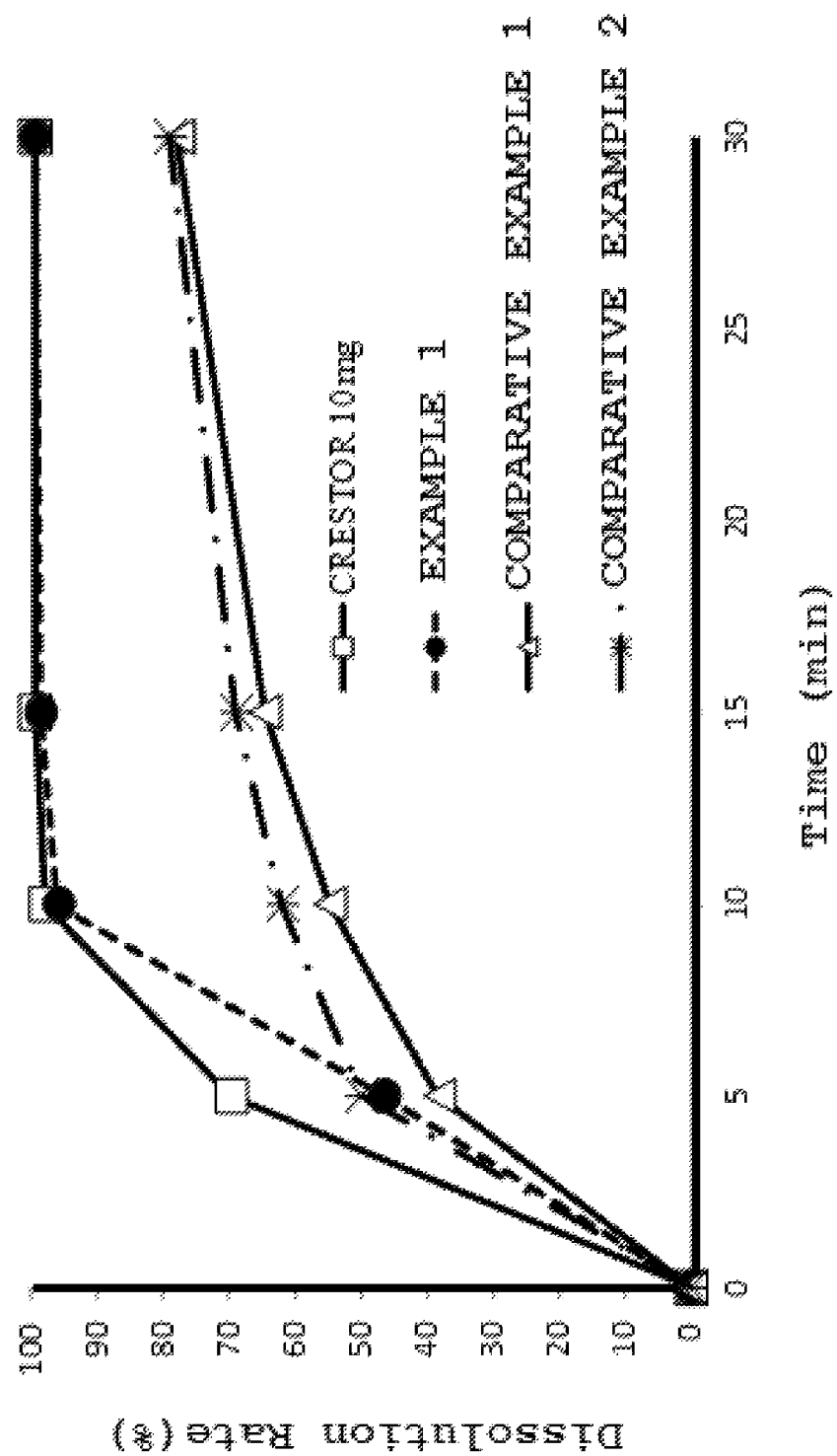

PHARMACEUTICAL COMBINATION DRUG

CROSS REFERENCE TO RELATED APPLICATIONS

This application is a National Stage of International Application No. PCT/KR2014/002178 filed Mar. 14, 2014, claiming priority based on Korean Patent Application No. 10-2013-0027114, filed Mar. 14, 2013, the contents of all of which are incorporated herein by reference in their entirety.

TECHNICAL FIELD

The present disclosure relates to a pharmaceutical combination preparation that dissolution is improved including fimasartan and rosuvastatin.

BACKGROUND ART

Apropos of hypertension, it is important to control blood pressure steadily below certain pressure because preventing coronary artery diseases such as stroke, cardiac failure and myocardial infarction, and cardiovascular complication such as renal insufficiency which threat life by keeping blood pressure in the normal range is more important than treating blood pressure directly. Selection of a therapeutic agent should be made carefully because therapeutic agent for blood pressure is required to be administered in long-term. Therefore, side effects incurred from long-term use of drug are needed to be reduced by combining drugs having different mechanisms rather than selecting only one drug and by reducing drug dosage via the combined administration for keeping blood pressure in the normal range over long periods.

However, there are problems such as decrease of medicinal effect and incurrence of side effects due to drug combination because absorption, metabolism, distribution, expression of drug effect, and excretion-related transporter, metabolic enzyme and gene of each drug have different property and show different actions when taking two or more ingredients. For instance, drug can cause problems in absorption, metabolism and excretion in everywhere at every phase such as the first phase of passing the intestinal wall, the second phase of influx into the liver, the third phase of activation via metabolized in the hepatocyte and the fourth phase of leakage from the hepatocyte through the biliary tract among others. Especially, disintegration and dissolution patterns of active ingredients according to pH cause a lot of problems in drug effectiveness when performing complex treatment.

Angiotensin II receptor blocker (ARB) is a drug effective in depressing blood pressure in both myocardial systole and diastole by blocking conjugation of angiotensin II which is one of the original substances that causes vasoconstriction with AT1 receptor among angiotensin receptors, and there are about 10 series of compound group including pharmaceutically acceptable salt. Also, these are being used for hypertension-related symptoms solely upon patients having mild through moderate symptoms or with angiotensin converting enzyme inhibitor which exhibits anti-hypertensive effect in similar mechanism [Angiotensin II Receptor Antagonist: An Overview, Am. J. Health-Syst. Pharm. 57(13): 1231-1238, 2000].

Fimasartan, one of the angiotensin II receptor blockers (ARB), is 2-n-butyl-5-dimethylaminothiocarbonylmethyl-6-methyl-3-[[2-(1H-tetrazol-5-yl)biphenyl-4-yl]methyl]pyrimidin-4(3H)-one and has a chemical formula 1, and it is approved under the title of KANARB® and currently available in the market (Korean Patent Registration No. 10-1058284).

[Chemical Formula 1]

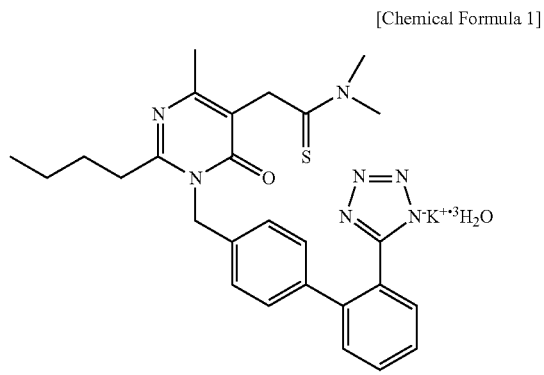

HMG-CoA reductase inhibitor has effects of decreasing blood lipid concentration and cholesterol by preventing the reduction of HMG-CoA to be mevalonate, and thus it is used for hyperlipidemia, hypercholesterolemia and atherosclerosis.

Rosuvastatin, one of the HMG-CoA (3-hydroxy-3-methylglutaryl-CoA) reductase inhibitor, is (E)-7-[4-(4-fluorophenyl)-6-isopropyl-2-[methyl(methylsulfonyl)amino]pyrimidin-5-yl]-(3R,5S)-3,5-dihydroxyhept-6-enoic acid and has a structure of chemical formula 2, and it controls synthetic pathway of cholesterol and it is approved under the title of CRESTOR® and currently available in the market (Korean Patent Registration No. 10-0105432).

[Chemical Formula 2]

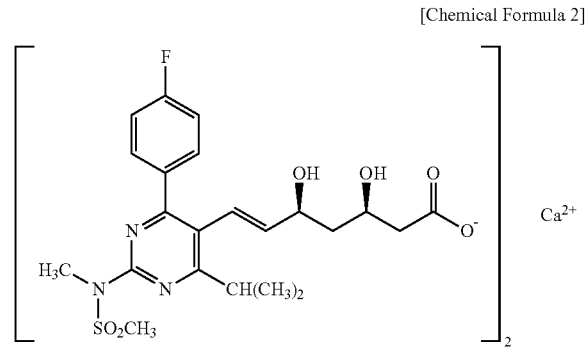

Fimasartan and rosuvastatin combination preparation having different acting mechanisms can be used for hypertension treatment but these combination preparation have a problem of affecting disintegration and dissolution of each active ingredient due to effect of interference to each other. That is, fimasartan exhibits decent solubility pattern under comparatively high pH media such as purified water and pH 6.8 dissolution media, but its solubility decreases under low pH media (i.e. pH 1.0-pH 4.0) and KANARB® which is a currently available fimasartan formulation in the market exhibits similar solubility pattern.

According to the properties of fimasartan explained above, problem of decreasing disintegration and dissolution due to interference between fimasartan and rosuvastatin is raised when preparing combination preparation with rosuvastatin. Especially, decrease of dissolution under low pH media could seriously affect bioavailability at the stomach where initial disintegration and dissolution occurs at the time of oral administration.

Under these circumstances, a research on a method of keeping constant disintegration and dissolution rates of fimasartan and rosuvastatin in spite of pH variation in the normal stomach is required.

SUMMARY OF INVENTION

Technical Problem

The present disclosure is related to a pharmaceutical combination preparation of fimasartan and rosuvastatin including meglumine. It is an object of the present disclosure to provide a superior combination preparation which increases disintegration and dissolution rate, to prevent drug interference and to ease taking of a drug with single administration.

Solution to Problem

The present disclosure provides pharmaceutical combination preparation including fimasartan, pharmaceutically acceptable salt thereof, isomer thereof, or hydrate or solvate thereof; rosuvastatin, pharmaceutically acceptable salt thereof, isomer thereof, or hydrate or solvate thereof; and meglumine.

The pharmaceutical combination preparation of the present disclosure is a superior combination preparation which greatly enhances disintegration and dissolution rates, prevents drug interference and eases taking of a drug with single administration, and has an advantage in superior bioavailability.

The pharmaceutical combination preparation of the present disclosure includes fimasartan, pharmaceutically acceptable salt thereof, isomer thereof, or hydrate or solvate thereof; rosuvastatin, pharmaceutically acceptable salt thereof, isomer thereof, or hydrate or solvate thereof as a pharmacological active ingredient. In the present disclosure, isomer includes optical isomer, diastereomer and mixture of both.

The fimasartan, pharmaceutically acceptable salt thereof, isomer thereof, or hydrate or solvate thereof can be included as 5.0 mg-240.0 mg in unit dosage form, preferably 5.0 mg-120.0 mg, and more preferably 30.0 mg-120.0 mg, and rosuvastatin, pharmaceutically acceptable salt thereof, isomer thereof, or hydrate or solvate thereof can be included as 5.0 mg-20.0 mg in unit dosage form. It is desirable to use fimasartan potassium which is a pharmaceutically acceptable salt of the fimasartan, and more preferably fimasartan potassium trihydrate and rosuvastatin calcium which is a pharmaceutically acceptable salt of the rosuvastatin as a pharmacological active ingredient.

The meglumine of the present disclosure is an amino sugar derived from sorbitol and has a structure as illustrated in the following chemical formula 3. The meglumine is an excipient of the present disclosure for inhibiting decrease of disintegration and dissolution due to interference of fimasartan and rosuvastatin, and exhibits effect of inhibiting interference of active ingredients and increases disintegration and dissolution rates. This meglumine can be included in the amount of 1.0-30.0 wt %, preferably 2.0-15.0 wt %, and more preferably 2.0-10.0 wt % based on the total weight of the combination preparation.

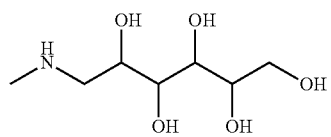

[Chemical Formula 3]

The pharmaceutical preparation of the present disclosure is for the prevention or treatment of cardiovascular diseases, and cardiovascular diseases include hypertension or all the symptoms such as hypertension and complication of the metabolic syndrome patients who comorbidly showing diabetes, obesity, hyperlipidemia, coronary arterial diseases among others, and also include chronic stable angina, vasospastic angina, stroke, myocardial infarction, transient ischemic attack, congestive heart failure, insulin resistance, impaired glucose tolerance, type 2 diabetes mellitus, diabetic nephropathy, dyslipidemia, cognitive impairments and dementia among others.

The combination preparation of the present disclosure can further include pharmaceutically acceptable additives pro re nata and can be formulated by including additives, for examples, such as stabilizer, binder, disintegrant, lubricant, diluents, coating agent, pH modifier, solubilizing agent and surfactant among others which are pharmaceutically acceptable within the scope of the effects of the present disclosure.

Dibasic or tribasic calcium phosphate, tribasic magnesium phosphate and tribasic aluminium phosphate among others can be used as the stabilizer. The stabilizer can be included in the amount of 1.0-50.0 wt %, preferably 2.0-30.0 wt %, and more preferably 2.0-10.0 wt % based on the total weight of the combination preparation.

Hydroxypropyl cellulose, hydroxypropyl methylcellulose, starch, gelatin, glucose syrup, polyvinyl pyrrolidone, polyethylene glycol 6000, methylcellulose, ethylcellulose, carboxymethylcellulose, or mixture thereof among others can be used as the binder. Preferably, the binder can include at least more than one substance selected from a group consisted of Hydroxypropyl cellulose, hydroxypropyl methylcellulose and polyvinyl pyrrolidone. Also, it is desirable to include the binder in the amount of 0.2-5.0 wt % and preferably 0.5-4.0 wt % based on the total weight of the combination preparation.

Starch or modified starch such as sodium starch glycolate, corn starch, potato starch or fully gelatinized starch among others; clay such as bentonite, montmorillonite or veegum among others; celluloses such as microcrystalline cellulose, hydroxypropyl cellulose or carboxymethylcellulose among others; algins such as sodium alginate or alginic acid among others; crosslinked celluloses such as croscarmellose sodium among others; gums such as guar gum, xanthan gum among others; crosslinked polymers such as crospovidone among others; effervescent agents such as sodium bicarbonate and citric acid among others, or mixture thereof can be used as the disintegrant. Preferably, the disintegrant can include mixture of the croscarmellose sodium and the crospovidone. Also, it is desirable to include the disintegrant in the amount of 2.0-30.0 wt % and preferably 5.0-20.0 wt % based on the total weight of the combination preparation.

Magnesium stearate, calcium stearate, stearic acid, sodium stearyl fumarate, polyethylene glycol or silicon dioxide can be used as the lubricant. It is desirable to include the lubricant in the amount of 0.2-5.0 wt % and preferably 0.5-3.0 wt % based on the total weight of the combination preparation.

Cellulose, lactose, starch, microcrystalline cellulose, lactose hydrate, glucose, mannitol, alginate, alkaline earth metal salt, clay, polyethylene glycol, dicalcium phosphate, or mixture thereof can be used as the diluents. The diluents can be included in the amount of 15.0-90.0 wt %, preferably 30.0-70.0 wt % and more preferably 35.0-65.0 wt % based on the total weight of the combination preparation.

Hydroxypropyl methylcellulose, ethylcellulose, polyvinyl acetate, polyethylene glycol, titanium dioxide, iron oxide among others or the product Opadry® can be included in the coating agent. The coating agent, for example, can be included in a tablet composition in the amount of 0.5-10.0 wt %, preferably 1.0-6.0 wt % and more preferably 2.0-5.0 wt %. It is desirable to coat tablets because the coating reduces photodegradation product formation rate of the drug and enhances storage stability of the product which can be affected by moisture and heat.

Alkalinizing agents such as precipitated calcium carbonate and aqueous ammonia can be used as the pH modifier.

Polyoxyethylene sorbitan fatty acid esters such as sodium lauryl sulfate and polysorbate, and docusate sodium among others can be used as the solubilizing agent.

Sodium lauryl sulfate, cremophor, poloxamer, docusate and pharmaceutically acceptable docusate salt among others can be used as the surfactant.

The formulation of the present disclosure also can be prepared by using various pharmaceutically acceptable additives selected from coloring agents and flavors, and available additives are not limited to those disclosed in the present disclosure. The additives can be formulated by including it within the range of conventional amount via selection.

The pharmaceutical combination preparation can be formulated as a formulation for oral administration in a form of a tablet such as an uncoated tablet, a coated tablet, a multi-layer tablet and a cored tablet, and powder, granules or a capsule.

For instance, the pharmaceutical preparation of the present disclosure can be a form of an uncoated tablet prepared through mixing granular part of the fimasartan and mixed part of the rosuvastatin and tableting it. The granular part of the fimasartan can be prepared by dry granulation method and wet granulation method, and prepared preferably by the wet granulation method.

In addition, the pharmaceutical preparation of the present disclosure can be a form of a coated tablet which further includes additional coating layer on the exterior of the granular part of the fimasartan and mixed part of the rosuvastatin.

A method of preparing a coating layer can be selected by those skilled in the art within the methods which can form a film-type coating layer on a surface of tablet layer pro re nata and methods such as fluid-bed coating, pan coating, dry coating among others can be applied.

In addition, the pharmaceutical preparation of the present disclosure can be a form of a cored tablet constituted of an external layer comprising mixed part of the rosuvastatin that surrounds inner core constituted of granular part of the fimasartan and exterior of the inner core.

Human dosage of the preparation of the present disclosure is properly selected according to intracorporeal absorption rate of active ingredient, inactivation rate, and excretion rate, age and sex of patients inter alia but generally 30.0-120.0 mg of fimasartan per a day and 5.0-20.0 mg of rosuvastatin per a day can be administered for adults to act as prevention and treatment of cardiovascular diseases.

Additionally, the present disclosure provides a pharmaceutical composition including the combination preparation. The pharmaceutical composition of the present disclosure has remarkable effect in preventing and treating cardiovascular diseases.

Further, the present disclosure provides a treatment method for cardiovascular diseases including administration of therapeutically effective dose of the combination preparation including fimasartan, pharmaceutically acceptable salt thereof, isomer thereof, or hydrate or solvate thereof; rosuvastatin, pharmaceutically acceptable salt thereof, isomer thereof, or hydrate or solvate thereof; and meglumine.

The treating method for cardiovascular diseases by using the combination preparation of the present disclosure includes administration of the combination preparation of the present disclosure in an amount of therapeutically effective dose. The term "therapeutically effective dose" stated in the present disclosure describes an amount of the combination preparation of the present disclosure that is effective in preventing or treating cardiovascular diseases. Cardiovascular diseases include hypertension or all the symptoms such as hypertension and complication of the metabolic syndrome patients who comorbidly showing hypertension, or diabetes, obesity, hyperlipidemia, coronary arterial diseases among others, and also include chronic stable angina, vasospastic angina, stroke, myocardial infarction, transient ischemic attack, congestive heart failure, insulin resistance, impaired glucose tolerance, type 2 diabetes mellitus, diabetic nephropathy, dyslipidemia, cognitive impairments and dementia among others. The combination preparation of the present disclosure can be applied to a treatment method by additionally combining it with one or more therapeutic agents.

Also, the present disclosure provides a use of the combination preparation including fimasartan, pharmaceutically acceptable salt thereof, isomer thereof, or hydrate or solvate thereof; rosuvastatin, pharmaceutically acceptable salt thereof, isomer thereof, or hydrate or solvate thereof; and meglumine for preparation of medicaments for cardiovascular disease treatment. The acceptable additives supra can be mixed with the combination preparation of the present disclosure for preparation of medicaments and for instance, the combination preparation can be prepared by including additives such as stabilizer, binder, disintegrant, lubricant, diluents, coating agent, pH modifier, solubilizing agent and surfactant among others which are pharmaceutically acceptable within the scope of the effects of the present disclosure.

In addition, the present disclosure provides a use for treating cardiovascular diseases by using the combination preparation including fimasartan, pharmaceutically acceptable salt thereof, isomer thereof, or hydrate or solvate thereof; rosuvastatin, pharmaceutically acceptable salt thereof, isomer thereof, or hydrate or solvate thereof; and meglumine.

Matters stated in regard of the combination preparation, composition, treatment method and use of the present disclosure are applied identically unless these are contradictory to each other.

Advantageous Effect

The pharmaceutical combination preparation of the present disclosure exhibits remarkable effect as a pharmaceutical combination preparation for prevention or treatment of cardiovascular diseases by resolving problems of delaying disintegration and dissolution due to interference of fimasartan and rosuvastatin in low pH media by using meglumine.

DESCRIPTION OF DRAWINGS

The FIGURE illustrates analysis result of dissolution pattern of the pharmaceutical combination preparation including fimasartan and rosuvastatin as active ingredient with meglumine.

DESCRIPTION OF THE PREFERRED EMBODIMENTS

The present disclosure will be described more fully hereinafter with reference to the accompanying preparational examples and experimental examples. However, the following preparational examples and experimental examples are intended to illustrate the present invention, and the present invention is not limited by the following preparational examples and experimental examples.

EXAMPLES

Preparation of Combination Tablet Including Meglumine

TABLE 1

Ingredients and Contents of the Combination Tablet Including Meglumine

Unit: mg/tablet

|  | Example 1 | Example 2 | Example 3 |
|---|---|---|---|
| Granular Part of the Fimasartan | | | |
| Fimasartan Potassium Trihydrate | 66.00 | 66.00 | 66.00 |
| Microcrystalline Cellulose | 72.75 | 72.75 | 72.75 |
| Croscarmellose Sodium | 7.50 | 7.50 | 7.50 |
| Hydroxypropyl Cellulose | 1.50 | 1.50 | 1.50 |
| Magnesium Stearate | 2.25 | 2.25 | 2.25 |
| Mixed Part of the Rosuvastatin | | | |
| Rosuvastatin Calcium | 10.40 | 10.40 | 10.40 |
| Microcrystalline Cellulose | 38.60 | 40.60 | 33.60 |
| Meglumine | 10.00 | 5.00 | 20.00 |
| Lactose Hydrate | 37.00 | 40.00 | 32.00 |
| Crospovidone | 2.00 | 2.00 | 2.00 |
| Magnesium Stearate | 2.00 | 2.00 | 2.00 |
| Total Weight (mg/tablet) | 250 | 250 | 250 |

1. Example 1

(1) Preparation of the Granular Part of the Fimasartan

The granular part of the fimasartan of Example 1 was prepared to have the same weight per unit dosage form to Table 1. Fimasartan potassium trihydrate was put into the part of the microcrystalline cellulose and mixed for about two minutes, and sieved through a No. 30 mesh screen twice. Put the sieved mixture, the rest of the microcrystalline cellulose and part of the croscarmellose sodium in a high speed mixer and mixed for about three minutes. Binder solution was separately prepared by dissolving hydroxypropyl cellulose in 65 mL of purified water.

The prepared binder solution was put into the high speed mixer, sieved through No. 20 mesh screen after wet granulation with a mixed solution, and dried. Fimasartan granules were prepared through putting the rest of the croscarmellose sodium in the dried granular part of the fimasartan and mixing in a double cone mixer for five minutes and supplementally mixing with the magnesium stearate for five minutes.

(2) Preparation of the Mixed Part of the Rosuvastatin

The mixed part of the rosuvastatin of Example 1 was prepared to have the same weight per unit dosage form to Table 1. Rosuvastatin calcium was put into the meglumine and part of the lactose and mixed for about two minutes, and sieved through a No. 30 mesh screen twice. Put the sieved mixture, the rest of the lactose, microcrystalline cellulose and crospovidone in a double cone mixer and mixed for about three minutes. Magnesium stearate was added as a lubricant and supplementally mixed for about five minutes.

(3) Tablet Compression

The combination preparation was prepared by tableting with 20 kN of tableting pressure by using a rotary tablet compression machine (PICCOLA DC, RIVA) to have 249~251 mg of weight (250.0 mg of theoretical weight) and 9~10 kp of hardness per one tablet. Friability of the tablets obtained through the above process was measured by using a friability tester (25 rpm, 100 free falls). The measured friability was 0.1% and below, and thus hardness of the tablets was fine.

2. Example 2

Altered the content of the meglumine to 5.0 mg and prepared tablets according to the contents of Table 1 via the same method explained in Example 1.

3. Example 3

Altered the content of the meglumine to 20.0 mg and prepared tablets according to the contents of Table 1 via the same method explained in Example 1.

COMPARATIVE EXAMPLES

Preparation of Combination Preparation Wherein Meglumine was not Included

TABLE 2

Ingredients and Contents of the Combination preparation wherein Meglumine was not included Unit: mg/tablet

|  | Comparative Example 1 | Comparative Example 2 |
|---|---|---|
| Granular Part of the Fimasartan | | |
| Fimasartan Potassium Trihydrate | 66.00 | 66.00 |
| Microcrystalline Cellulose | 72.75 | 72.75 |
| Croscarmellose Sodium | 7.50 | 7.50 |
| Hydroxypropyl Cellulose | 1.50 | 1.50 |
| Magnesium Stearate | 2.25 | 2.25 |

TABLE 2-continued

Ingredients and Contents of the Combination
preparation wherein Meglumine was not included Unit: mg/tablet

| | Comparative Example 1 | Comparative Example 2 |
|---|---|---|
| Mixed Part of the Rosuvastatin | | |
| Rosuvastatin Calcium | 10.40 | 10.40 |
| Microcrystalline Cellulose | 43.60 | 41.60 |
| Meglumine | — | — |
| Lactose Hydrate | 42.00 | 41.00 |
| Crospovidone | 2.00 | — |
| Croscarmellose Sodium | — | 5.00 |
| Magnesium Stearate | — | 2.00 |
| Total Weight (mg/tablet) | 250 | 250 |

1. Comparative Example 1

(1) Preparation of the Granular Part of the Fimasartan

The granular part of the fimasartan of Comparative Example 1 was prepared to have the same weight per unit dosage form to Table 2. Fimasartan potassium trihydrate was put into the part of the microcrystalline cellulose and mixed for about two minutes, and sieved through a No. 30 mesh screen twice. Put the sieved mixture, the rest of the microcrystalline cellulose and part of the croscarmellose sodium in a high speed mixer and mixed for about three minutes. Binder solution was separately prepared by dissolving hydroxypropyl cellulose in purified water. The prepared binder solution was put into the high speed mixer, sieved through No. 20 mesh screen after wet granulation with a mixed solution, and dried. Fimasartan granules were prepared through putting the rest of the croscarmellose sodium in the dried granular part of the fimasartan and mixing in a double cone mixer for five minutes and supplementally mixing with the magnesium stearate for five minutes.

(2) Preparation of the Mixed Part of the Rosuvastatin

The tablet of Comparative Examples was prepared to have the same weight per unit dosage form to Table 2. Rosuvastatin calcium was put into the part of the lactose and mixed for about two minutes, and sieved through No. 30 mesh screen twice. Put the sieved mixture, the rest of the lactose, microcrystalline cellulose and the crospovidone (Comparative Example 1) in a double cone mixer and mixed for about three minutes. Magnesium stearate was added as a lubricant and supplementally mixed for about five minutes.

(3) Tablet Compression

The combination preparation was prepared by tableting with 20 kN of tableting pressure by using a rotary tablet compression machine (PICCOLA DC, RIVA) to have 249-251 mg of weight (250.0 mg of theoretical weight) and 9-10 kp of hardness per one tablet. Friability of the tablets obtained through the above process was measured by using a friability tester (25 rpm, 100 free falls). The measured friability was below 0.1% and thus hardness of the tablets was fine.

2. Comparative Example 2

Prepared Comparative Example 2 via the same preparation method explained in Comparative Example 1 with the compositions of Table 2 except an alteration of the disintegrant from crospovidone to croscarmellose sodium.

EXPERIMENTAL EXAMPLE

Dissolution Test in the Combination Preparation of Fimasartan and Rosuvastatin

A dissolution test for the combination preparation of fimasartan potassium trihydrate and the rosuvastatin calcium obtained through Example 1 and Comparative Examples 1-2 and the CRESTOR® currently available in the market were conducted under conditions stated in Table 3 below and the test result was illustrated in the FIGURE.

TABLE 3

Conditions for dissolution test and HPLC analyzing

| Effluent | pH 1.2 dissolution medium, 900 mL |
|---|---|
| Method | usp paddle method, 50 rpm |
| Temperature | 37 ± 0.5° C. |
| Column | $C_{18}$ (5 microns, 150 * 4.6 mm) |
| Apparatus | Detection 260 nm, 242 nm |
| | Temperature 40° C. |
| | Run time 30 min |
| | Injection 20 uL |
| | Flow rate 1.0 mL/min |
| | Sample Temp. 5° C. |
| Mobile phase | Water:Acetonitrile:1 vol % Trifluoroacetic acid(57:42:1, v/v/v) |

As illustrated in the FIGURE, interference of fimasartan and rosuvastatin in Example 1 was remarkably low compared to the other formulations and thus it was shown that disintegration and dissolution were highly increased, and effects thereof was almost identical with the CRESTOR® on market as a single agent. However, disintegration and dissolution rates of Comparative Example wherein meglumine was not included were extremely low due to interference.

It is understood that the combination preparation of fimasartan and rosuvastatin including meglumine has superior bioavailability based on the above result.

INDUSTRIAL APPLICABILITY

As explained hereinbefore, the combination preparation of the present disclosure can be safely and effectively used for prevention and treatment of cardiovascular diseases.

The invention claimed is:

1. A pharmaceutical combination preparation comprising a granular part of fimasaratan and a mixed part of rosuvastatin,
    wherein the granular part of fimasartan comprises a fimasartan, a pharmaceutically acceptable salt thereof, an isomer thereof, or a hydrate or a solvate thereof; and
    wherein the mixed part of rosuvastatin comprises a rosuvastatin, a pharmaceutically acceptable salt thereof, an isomer thereof, or a hydrate or a solvate thereof; and a meglumine.

2. The pharmaceutical combination preparation according to claim 1, wherein the pharmaceutically acceptable salt of the fimasartan is a fimasartan potassium.

3. The pharmaceutical combination preparation according to claim 1, wherein the hydrate of the fimasartan is a fimasartan potassium trihydrate.

4. The pharmaceutical combination preparation according to claim 1, wherein the fimasartan, the pharmaceutically acceptable salt thereof, the isomer thereof, or the hydrate or the solvate thereof is contained in an amount of 5.0 mg-240.0 mg per unit dosage form.

5. The pharmaceutical combination preparation according to claim 1, wherein the rosuvastatin, the pharmaceutically acceptable salt thereof, the isomer thereof, or the hydrate or the solvate thereof is a rosuvastatin calcium.

6. The pharmaceutical combination preparation according to claim 1, wherein the rosuvastatin is contained in an amount of 5.0 mg-20.0 mg per unit dosage form.

7. The pharmaceutical combination preparation according to claim 1, wherein the meglumine is contained in an amount of 1.0-30.0 wt % based on the total weight of the combination preparation.

8. The pharmaceutical combination preparation according to claim 1, wherein the combination preparation is for a treatment of a cardiovascular disease.

9. The pharmaceutical combination preparation according to claim 8, wherein the cardiovascular disease is selected from the group consisting of hypertension, diabetes, obesity, hyperlipidemia, coronary arterial diseases, chronic stable angina, vasospastic angina, stroke, myocardial infarction, transient ischemic attack, congestive heart failure, insulin resistance, impaired glucose tolerance, preliminary diabetes, type 2 diabetes mellitus, diabetic nephropathy, dyslipidemia, cognitive impairments, dementia and combinations thereof.

10. The pharmaceutical combination preparation according to claim 1, further comprising at least one of a stabilizer, a binder, a disintegrant or a lubricant.

11. The pharmaceutical combination preparation according to claim 10, wherein the stabilizer is contained in an amount of 1.0-50.0 wt % based on the total weight of the combination preparation.

12. The pharmaceutical combination preparation according to claim 10, wherein the binder is contained in an amount of 0.2-5.0 wt % based on the total weight of the combination preparation.

13. The pharmaceutical combination preparation according to claim 10, wherein the disintegrant is contained in an amount of 2.0-30.0 wt % based on the total weight of the combination preparation.

14. The pharmaceutical combination preparation according to claim 10, wherein the lubricant is contained in an amount of 0.2-5.0 wt % based on the total weight of the combination preparation.

15. The pharmaceutical combination preparation according to claim 10, wherein the diluent is contained in an amount of 15.0-90.0 wt % based on the total weight of the combination preparation.

16. The pharmaceutical combination preparation according to claim 1, wherein the combination preparation is in a form of a tablet.

17. The pharmaceutical combination preparation according to claim 16, wherein the combination preparation is a form of a coated tablet which additionally comprises a coating layer on the exterior.

18. A pharmaceutical composition comprising the combination preparation according to claim 1.

19. A method of treating a cardiovascular disease comprising administration of a therapeutically effective dose of the combination preparation according to claim 1.

20. The method of treating cardiovascular diseases according to claim 19, wherein the cardiovascular diseases is selected from the group consisting of hypertension, diabetes, obesity, hyperlipidemia, coronary arterial diseases, chronic stable angina, vasospastic angina, stroke, myocardial infarction, transient ischemic attack, congestive heart failure, insulin resistance, impaired glucose tolerance, preliminary diabetes, type 2 diabetes mellitus, diabetic nephropathy, dyslipidemia, cognitive impairments, dementia and combinations thereof.

* * * * *